United States Patent
Strawder et al.

(10) Patent No.: US 6,779,524 B2
(45) Date of Patent: Aug. 24, 2004

(54) MOLDABLE SCENTED FACE MASK

(76) Inventors: Steffi A. Strawder, 117 Arbor Cove, Clinton, MS (US) 39056; Regina Thompson, 138 Carriage Hill, Jackson, MS (US) 39209

( * ) Notice: Subject to any disclaimer, the term of this patent is extended or adjusted under 35 U.S.C. 154(b) by 0 days.

(21) Appl. No.: 10/338,702

(22) Filed: Jan. 9, 2003

(65) Prior Publication Data

US 2003/0127102 A1 Jul. 10, 2003

Related U.S. Application Data

(60) Provisional application No. 60/346,626, filed on Jan. 10, 2002.

(51) Int. Cl.[7] .............................................. A62B 18/02
(52) U.S. Cl. .............................. 128/206.21; 128/206.26
(58) Field of Search ....................... 128/201.17, 201.23, 128/201.25, 202.28, 202.29, 203.11, 203.29, 204.12, 205.25, 205.27, 205.28, 205.29, 206.12–206.19, 206.21, 206.23, 206.24, 206.26, 206.27, 206.28, 207.13

(56) References Cited

U.S. PATENT DOCUMENTS

| | | | |
|---|---|---|---|
| 2,917,045 A | * 12/1959 | Schildknecht et al. . | 128/206.24 |
| 4,283,011 A | * 8/1981 | Spector ........................ | 239/36 |
| D270,110 S | 8/1983 | Moore et al. | |
| 4,419,396 A | * 12/1983 | Sugimoto ................... | 428/40.2 |
| D273,145 S | 3/1984 | Ponsi | |
| 4,503,851 A | * 3/1985 | Braunroth .............. | 128/203.29 |
| 4,683,588 A | 7/1987 | Goldberg | |
| 4,896,666 A | 1/1990 | Hinkle | |
| D323,908 S | 2/1992 | Hollister et al. | |
| 5,243,708 A | 9/1993 | Vanuch | |
| 5,357,947 A | 10/1994 | Adler | |
| 5,429,683 A | 7/1995 | Le Mitouard | |
| 5,538,013 A | * 7/1996 | Brannon ..................... | 128/857 |
| 5,697,105 A | * 12/1997 | White .......................... | 2/206 |
| D388,873 S | 1/1998 | Richards et al. | |
| 5,809,577 A | * 9/1998 | Getz ............................ | 2/406 |
| 5,921,239 A | 7/1999 | McCall et al. | |
| 5,975,079 A | 11/1999 | Hellings et al. | |
| D440,302 S | 4/2001 | Wolfe | |
| D442,276 S | 5/2001 | Geist | |
| D443,927 S | 6/2001 | Chen | |
| 2003/0145859 A1 | * 8/2003 | Bohn et al. ............ | 128/206.24 |

OTHER PUBLICATIONS

Daniel Annequin, MD et.al., "Fixed 50% Nitrous Oxide Oxygen Mixture for Painful Procedures: A French Survey", Pediatrics vol. 105 No. 4 Apr. 2000, p.e 47.*
"Bubbles the Fish" Pediatric Aerosol Mask, PARI Respiratory Equipment, Inc.*
1995 Blue Chip Community Business Award Winner, "Listening to the Customers" King Systems.*
Mirage® Full Face Mask Components, (1 page).

* cited by examiner

Primary Examiner—Henry Bennett
Assistant Examiner—Teena Mitchell
(74) Attorney, Agent, or Firm—Jacobson Holman PLLC

(57) ABSTRACT

Conforming, moldable face mask having a scented icon that can be activated to camouflage unpleasant odors emanating from the construction material of the mask and gases delivered therein. The mask is also moldable and conforming, thereby making it adjustable to recipient facial contours. It is provided in various shapes and sizes to conform to the facial features and dimensions of patients and users.

5 Claims, 2 Drawing Sheets

MOLDABLE SCENTED FACE MASK

This is a complete application claiming benefit of provisional No. 60/346,626, filed Jan. 10, 2002.

FIELD OF THE INVENTION

The present invention is concerned with any field that would require a face mask, and more specifically, the present invention is concerned with face masks that are fabricated with scented icons attached thereto in order to camouflage any unpleasant odors emanating from the mask or gases delivered through such masks. In addition, the mask is conformable and moldable to be able to snugly fit even the most difficult facial features. It must be noted that these moldable masks may contain a non-scented icon also for the recipients who are sensitive to certain fragrances.

BACKGROUND OF THE INVENTION

Face masks are used in the medical profession, such as for anesthesia and respiratory services. The face mask delivers gases to a patient before and during surgery and air or oxygen to a recipient to assist in breathing or respiration.

An anesthesia or oxygen delivery system is comprised of a source, such as a pressurized receptacle containing the anesthetic or respiratory gases, regulating valves and connector line or hose, and a face mask. The face mask is generally circular or slightly oval in shape and is comprised of a front-facing body, cushioned seal attached to the edge of the body, and a connector or portal attached to the exterior of the body for receipt of a connector line or hose. A flexible, resilient strap is attached at opposing ends thereof to the face mask to secure the face mask to the head of a patient or user.

Various improvements to face masks have been accomplished in design and consist of means to recapture escaped gas, more comfortable and effective cushioned seals, enhanced attachment straps, and mask design and shape that minimizes facial and ocular pressure. While such advances have improved the performance of the face masks, many patients and users still find it difficult to use face masks with any degree of comfort. For instance, face masks are manufactured of materials such as rubber, plastic, or other synthetic compounds that continuously emit an odor that some patients or users find unpleasant. Furthermore, the gases delivered to the face mask comprise potent volatile agents that patients may find disagreeable in smell, which, when combined with the odors emitted by a face mask, may cause an acutely disagreeable experience for the patient or user of the face mask. Further, certain face masks are stiff, nonconforming to the face thereby causing ocular and facial pressure to the recipient.

Numerous designs for face masks have been provided in the prior art. Even though these designs may be suitable for the specific individual purposes to which they address, they would not be suitable for the purposes of the present invention. Such designs are exemplified by U.S. Pat. No. 5,429,683, Face Mask For Breathing, issued to Le Mitouard on Jul. 4, 1995; U.S. Pat. No. 5,921,239, Face Mask For Patient Breathing, issued to McCall et al. on Jul. 13, 1999; U.S. Pat. No. 5,975,079, Anesthesia and Respiratory Face Mask, issued to Hellings et al. on Nov. 2, 1999; and U.S. Pat. No. 5,243,708, Disposable Scented Mask, issued to Vanuch on Sep. 14, 1993.

SUMMARY OF THE INVENTION

As such, it may be appreciated that there is a continuing need for a new and improved conforming, moldable face mask having a scented icon that can be activated to camouflage unpleasant odors emanating from the construction material of the mask and gases delivered therein. The mask is also moldable and conforming, thereby making it adjustable to recipient facial contours. It is provided in various shapes and sizes to conform to the facial features and dimensions of patients and users. In these respects, the present version of the invention substantially departs from the conventional concepts and designs of the prior art, and in so doing provides an apparatus that substantially fulfills this need. Additionally, the prior patents and commercial techniques do not suggest the present inventive combination of component elements arranged and configured as disclosed herein.

What is needed then to overcome the aforementioned disadvantages of conventional face masks is the provision of a scented conforming face mask that is fabricated with a pleasing scent embedded in a familiar icon attached to the face mask. Also, the mask should be moldable or conforming to a recipient's facial features. This moldability may be achieved by forming the mask from polyethylene. Moldable masks will be able to better fit recipients with various facial shapes and features such as edentulous, small mouth, prominent nose, flat nose, receding jaw, etc.

The present invention achieves its intended purposes, objects, and advantages through a new, useful and unobvious combination of method steps and component elements, with the use of a minimum number of functioning parts, at a reasonable cost to manufacture, and by employing only readily available materials.

The present version of the invention, which will be described in greater detail hereinafter, relates to any field where a face mask is required. More specifically, this version of the invention is concerned with face masks that are moldable, conformable and fabricated with scented icons attached thereto in order to camouflage any unpleasant odors emanating from the mask or gases delivered through such masks. The present invention overcomes all of the shortcomings listed previously, in addition to novel aspects that will be described in detail hereinafter.

Described briefly, according to a typical embodiment, the invention presents a face mask having a scented icon affixed thereon having a pleasing scent. The face mask is generally circular in shape so as to conform to the facial characteristics of a user, typically covering the face from the bridge of the nose to under the mouth. It is comprised of a transparent or translucent body and a cushioned seal, which is affixed to the edge of the body. A tube connector is located on the front side of the body and receives a tube for delivery of gas into the interior of the mask. Rectangular apertures are located at opposing lateral sides of the body and receive the ends of a flexible, resilient head strap. The material of construction is latex free, and the transparent body may be provided in a variety of attractive colors. It must be noted that this face mask may be moldable with a scented icon, moldable with a nonscented icon, nonmoldable with scented icon or nonmoldable with nonscented icon.

A scented or nonscented icon is located on the interior of the body, such as a candy cane, fruit, and cartoon characters, for example. The candy cane icon, for instance, will release a peppermint scent and banana icon will release a banana scent. The masks are also moldable and conformable in order to accommodate patients and users with particular facial features, such as edentulous, prominent nose, flat nose, receding jaw, and the like. It must be noted that the mask is scented with a fragrant chemical or perfume layer applied directly to the icon on the interior of the mask.

The present invention, therefore, resides not in any one of these features per se, but rather in the particular combination of all of them herein disclosed. It is distinguished from the prior art in this particular combination of all of its structures for the functions specified.

In order that the detailed description of the invention may be better understood and that the present contribution to the art can be more fully appreciated, additional features of the invention will be described hereinafter. It should be appreciated by those of ordinary skill in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the present invention.

In this respect, before explaining at least a preferred embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention.

Accordingly, it is an object of the present invention to provide a low-cost, easy-to-manufacture, and easy-to-market face mask.

A further object of the present invention is to provide an easy-to-use and conformable moldable face mask.

A significant object of the present invention is to provide a face mask that is comprised of a transparent or translucent tinted body, moldable, cushioned seal attached to an edge of the body, tube connector, and a scented (or nonscented) icon attached to the body.

Still a further object of the present invention is to provide a prescented icon, which does not require scratching or rubbing of the icon to present a scent.

For a better understanding of the invention, its operating advantages and the specific objects attained by its uses, reference should be made to the accompanying drawings and descriptive matter in which there are illustrated preferred embodiments of the invention. The foregoing has outlined some of the more pertinent objects of the invention. These objects should be construed to be merely illustrative of some of the more prominent features and applications of the present invention. Many other beneficial results can be attached by applying the disclosed invention in a different manner or by modifying the invention within the scope of the disclosure. Accordingly, other objects and a fuller understanding of the invention may be had by referring to the summary of the invention and the detailed description of the preferred embodiments in addition to the scope of the invention illustrated by the accompanying drawings.

BRIEF DESCRIPTION OF THE DRAWINGS

The foregoing and other objects, features and advantages of the invention will become more fully understood from the following description of the preferred embodiments of the invention as illustrated in the accompanying drawings in which like reference characters refer to the same parts throughout different views. The drawings are not necessarily to scale, emphasis instead being placed upon illustrating the principles of the invention.

DETAILED DESCRIPTION OF THE PREFERRED EMBODIMENTS

Figure 1:
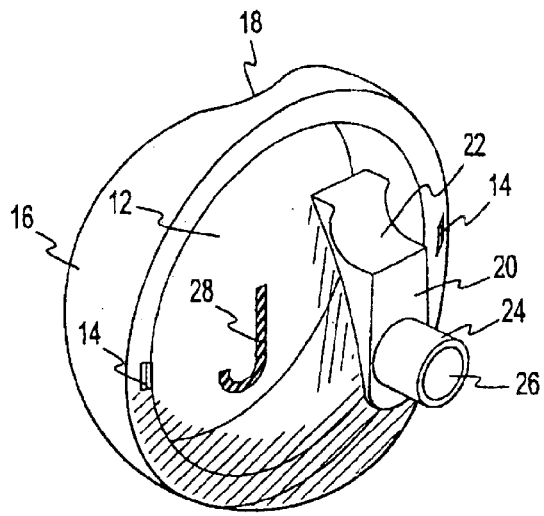
FIG. 1 is a perspective view of a scented, moldable face mask displaying a first icon in accordance with the present version of the invention.

Referring now to the drawings and, in particular, to FIG. 1 wherein there is illustrated a first embodiment of the face mask 10. The present version of the mask 10 of the present invention consists of a ovular body 12 with opposing rectangular apertures 14 and a cushioned seal 16. The cushioned seal 16 is affixed to the edge of the body 12 and is comprised of an outer layer of flexible, moldable material and an inner core of soft, resilient material such as sponge or foam. A slightly arcuate indentation 18, which is located at the top of the cushioned seal 16, receives the bridge of the nose of a patient or user when the mask 10 is in use. A tube connector 20 is located on the front of the body 12 and is comprised of a semi-circular indentation 22 and a cylindrical member 24 with bore 26. A tube or hose (not shown) is inserted into the bore 26 so that gas can be delivered into the interior of the mask for intake by a patient or user. A flexible, resilient head strap (not shown) is attached at opposing ends to the mask 10 at the apertures 14.

The body 12 is fabricated of material that is moldable, transparent or translucent and tinted with one of various pleasing colors so that a medical professional can view the interior of the mask 10 to monitor mucous, secretions, and respiration of the patient or user. Furthermore, all components 12, 16, 20 of the mask 10 employ material that is latex-free so as not to engender allergic reaction on the part of the patient or medical professional.

An icon 28 representing a candy cane, in this embodiment, is located on the interior of the body 12 adjacent to the tube connector 20. The icon 28 is scented with a scent normally associated with the icon and in this instance is peppermint scented. The scent may be comprised of well known or popular chemical or natural flavorings or compounds thereof in order to camouflage any unpleasant odors emanating from the face mask 10 or gases delivered therein so as to provide a pleasing olfactory response on the part of the patient or user of the face mask 10.

Figure 2:
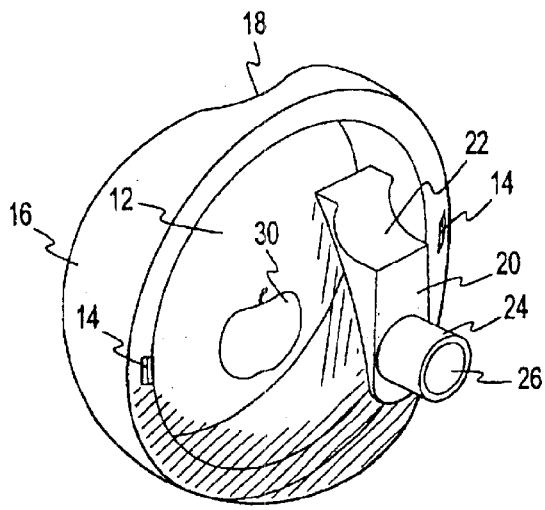
FIG. 2 is a perspective view of a scented, moldable face mask displaying a second icon in accordance with the present version of the invention.
Figure 3:
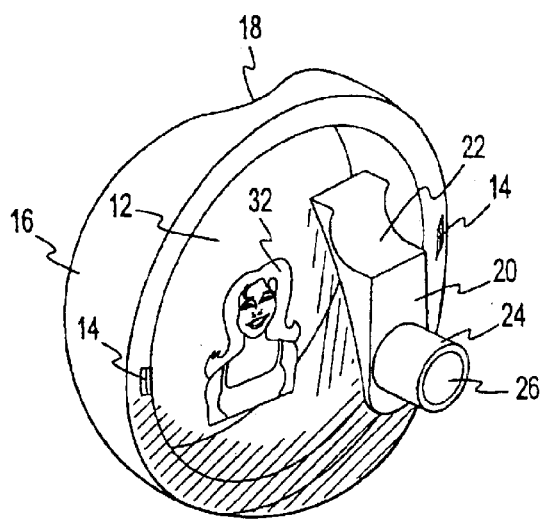
FIG. 3 is a perspective view of a scented, moldable face mask displaying a third icon in accordance with the present version of the invention.

Referring to FIG. 2, therein illustrated is the face mask 10 with an apple icon 30 located on the interior of the body 12 thereof adjacent to the tube connector 20. The icon 30 includes the scent of an apple. In FIG. 3, the face mask 10 is displayed with the icon 32 of a popular cartoon character (e.g. BARBIE doll), and the scent 32 may resemble perfume or the like.

In other types of masks, such as premie, neonate or infant mask, suitable icons and their normally associated scents, such as milk scented and juice scented for a bottle icon, may be used.

Figure 4:
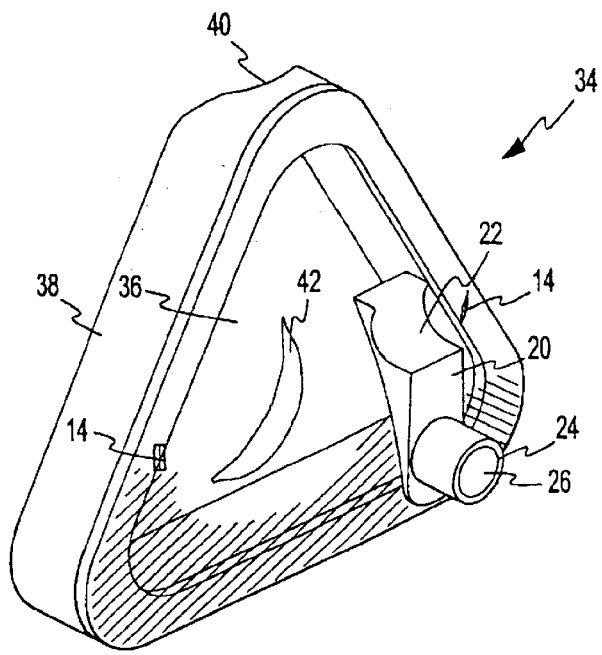
FIG. 4 is a perspective view of a scented, moldable face mask displaying an icon in accordance with the present version of the invention.

Face mask 34 is displayed in FIG. 4 wherein the face mask 34 is comprised of a transparent or translucent, tinted moldable body 36 with rectangular apertures 14, cushioned seal 38 with indentation 40, and tube connector 20. An icon 42 of a banana is located on the interior of the body. The icon 42 is infused with the scent of a banana.

Figure 5:
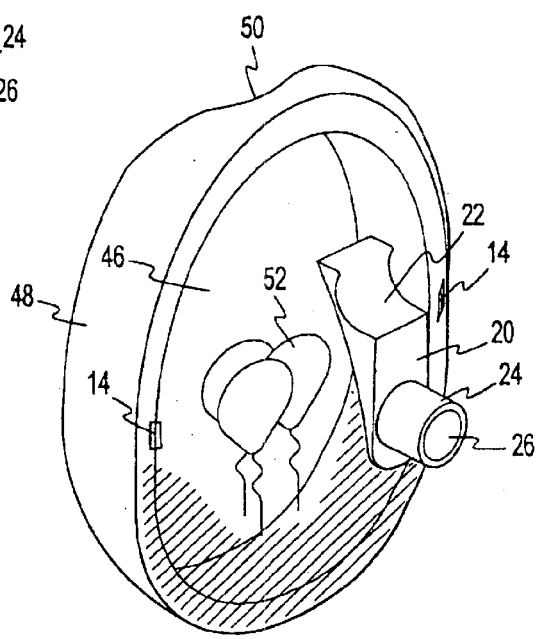
FIG. 5 is a perspective view of a scented, moldable face mask displaying an icon in accordance with the present version of the invention.

Face mask 44 is illustrated as having an oval shape in FIG. 5. The mask 44 is comprised of an oval transparent or translucent moldable tinted body 46 with rectangular apertures 14, oval cushioned seal with indentation 50, and tube connector 20. An icon 52 of a group of balloons is situated in the interior of the body 46. The icon 52 has a pleasing scent, such as that of candy fruit, potpourri, or the like.

Figure 6:
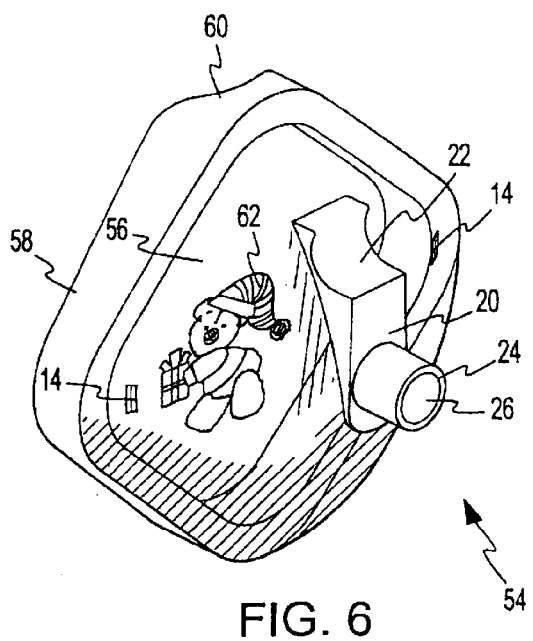
FIG. 6 is a perspective view of a scented, moldable face mask displaying an icon in accordance with the present version of the invention.

Face mask 54, illustrated in FIG. 6, is provided having a diamond shaped, tinted or translucent moldable body 56 with rectangular apertures 14, seal 58 with indentation 60, and a tube connector 20 located in the interior of body 56. An icon 62 representing a cartoon character is located in the interior of the body 20 for releasing a pleasing scent, such as that of candy, fruit, potpourri, or the like.

The face masks 10, 34, 44, 54 are furnished in both adult and pediatric sizes, and icons may be interchanged on masks or combined onto one mask. For instance, a mask may have both the apple 30 located interiorly and balloon 52 icons exteriorly or a combination of other icons referenced in this description or icons not referenced but intended to be covered by the spirit and scope of this version of the invention, such as icons representing bubble gum, cherry, strawberry, coconut, orange, grape, peach, etc.

Similarly, it is considered as being within the scope of the present invention to have icons which are removably sealed to an interior or exterior of the face mask. An adhesive layer may be used to secure the icon. Therefore, a patient may have the option of picking an icon which would make them the most comfortable and by providing a scent associated with the icon, the present invention may be able to put a patient at ease while masking or camouflaging any unpleasant odors normally encountered from gases or the mask themselves.

While this version of the invention has been illustrated and described in detail in the drawings and foregoing description, the same is to be considered as illustrative and not restrictive in character, it being understood that all changes and modifications that come within the spirit of the version of the invention are desired to be protected. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

From the foregoing, it will be understood by persons of ordinary skill in the art that an improved face mask has been provided, consisting of a variety of shapes and incorporating scented icons, which release pleasing scents. In addition, this mask conforms to the facial features of the wearer. The invention is relatively simple and easy to manufacture, yet affords a variety of uses. While the description contains many specificities, these should not be construed as limitations on the scope of the version of the invention, but rather as an exemplification of the preferred embodiments thereof. The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention. Although this invention has been described in its preferred form with a certain degree of particularity, it is understood that the present disclosure of the preferred form has been made only by way of example and numerous changes in the details of construction and combination and arrangement of parts may be resorted to without departing from the spirit and scope of the invention.

We claim:

1. A face mask for covering a mouth and nose of a face of a wearer, said face mask comprising:
   a body, said body being made of a moldable material so as to be conformable to a shape of the face of a wearer for sealing around the nose and the mouth of the wearer regardless of facial features, said body being at least translucent and defining an interior surface to be located adjacent the face of the wearer and an exterior surface located on an opposite side of the body from the interior surface, and
   an icon integral with the body for providing a calming appearance to the wearer, said icon being located on the interior surface of the body and including a scent.

2. A face mask as claimed in claim 1, wherein the scent is associated with an appearance provided by the icon to provide a smell characteristic of the icon.

3. A face mask as claimed in claim 2, wherein the icon is removably mounted on the body.

4. A face mask as claimed in claim 1, wherein the body includes a tubular access to the interior surface of the body.

5. A face mask for covering a mouth and nose of a face of a wearer, said face mask comprising:
   a body, said body being made of a moldable material so as to be conformable to a shape of the face of a wearer for sealing around the nose and the mouth of the wearer regardless of facial features, said body being at least translucent and defining an interior surface to be located adjacent the face of the wearer and an exterior surface located on an opposite side of the body from the interior surface,
   an icon integral with the body on the interior surface of the body for providing a calming appearance to the wearer, and
   a scent characteristic of an appearance of the icon being included in the body.

* * * * *